(12) United States Patent
Blach et al.

(10) Patent No.: US 6,676,681 B1
(45) Date of Patent: Jan. 13, 2004

(54) REUSABLE NASAL SUPPORT DEVICES FOR ANIMALS AND METHODS

(75) Inventors: Edward L. Blach, Roswell, NM (US); James R. Chiapetta, Eagan, MN (US)

(73) Assignee: Winease LLC, Eagan, MN (US)

( * ) Notice: Subject to any disclaimer, the term of this patent is extended or adjusted under 35 U.S.C. 154(b) by 192 days.

(21) Appl. No.: 09/713,380

(22) Filed: Nov. 15, 2000

Related U.S. Application Data

(60) Provisional application No. 60/165,578, filed on Nov. 15, 1999.

(51) Int. Cl.[7] ............................................. A61M 29/00
(52) U.S. Cl. ................... 606/199; 128/200.24
(58) Field of Search ............... 606/204.45, 199, 606/201; 128/200.24; 602/47, 59, 54, 74

(56) References Cited

U.S. PATENT DOCUMENTS

| | | | |
|---|---|---|---|
| 1,232,956 A | | 7/1917 | Mooney |
| 5,383,891 A | * | 1/1995 | Walker ........................ 606/196 |
| 5,476,091 A | | 12/1995 | Johnson |
| 5,533,499 A | | 7/1996 | Johnson |
| 5,533,503 A | | 7/1996 | Doubek et al. |
| 5,546,929 A | | 8/1996 | Muchin |
| 5,549,103 A | | 8/1996 | Johnson |
| 5,553,605 A | | 9/1996 | Muchin |
| RE35,408 E | | 12/1996 | Petruson |
| 5,611,333 A | | 3/1997 | Johnson |
| 5,653,224 A | | 8/1997 | Johnson |
| 5,669,377 A | | 9/1997 | Fenn |
| 5,706,800 A | | 1/1998 | Cronk et al. |
| 5,718,224 A | | 2/1998 | Muchin |
| 5,755,232 A | | 5/1998 | Kalt |
| 5,765,548 A | | 6/1998 | Perry |
| 5,769,089 A | * | 6/1998 | Hand et al. .................. 128/858 |
| 5,842,469 A | | 12/1998 | Rapp et al. |
| 5,890,486 A | | 4/1999 | Mitra et al. |
| 5,913,873 A | | 6/1999 | Blach et al. |
| 5,947,119 A | | 9/1999 | Reznick |
| 5,957,126 A | | 9/1999 | Neeser |
| 5,961,537 A | * | 10/1999 | Gould .................... 606/204.45 |
| 5,976,173 A | | 11/1999 | Berke |
| 6,017,357 A | | 1/2000 | Blach et al. |
| 6,033,422 A | * | 3/2000 | Blach et al. ................. 606/199 |
| 6,065,470 A | * | 5/2000 | Van Cromvoirt et al. ...................... 128/200.24 |
| 6,098,616 A | * | 8/2000 | Lundy, Jr. et al. ....... 128/200.24 |
| D432,652 S | * | 10/2000 | Ierulli ........................ D24/135 |
| 6,203,560 B1 | * | 3/2001 | Blach et al. ................. 606/199 |
| 6,228,101 B1 | * | 5/2001 | Stratton ........................ 606/199 |
| 6,352,548 B1 | * | 3/2002 | Blach et al. ................. 606/199 |
| 6,453,901 B1 | | 9/2002 | Ierulli |
| 6,540,766 B2 | * | 4/2003 | Martino ........................ 606/199 |

FOREIGN PATENT DOCUMENTS

| | | |
|---|---|---|
| AU | 702632 | 4/1998 |
| ES | 289561 | 10/1985 |
| GB | 768488 | 2/1957 |
| GB | 2 313 313 | 11/1997 |
| WO | WO 92/22340 | 12/1992 |
| WO | WO 94/23675 | 10/1994 |
| WO | WO 97/02793 | 1/1997 |
| WO | WO 98/12998 | 4/1998 |
| WO | WO 98/47451 | 10/1998 |

\* cited by examiner

*Primary Examiner*—A. Vanatta
*Assistant Examiner*—Alissa L Hoey
(74) *Attorney, Agent, or Firm*—Merchant & Gould P.C.

(57) ABSTRACT

The present invention is directed to nasal support devices and methods. In particular, the invention provides reusable nasal support devices and method for animals.

12 Claims, 3 Drawing Sheets

REUSABLE NASAL SUPPORT DEVICES FOR ANIMALS AND METHODS

This application claims the benefit of Provisional Application Ser. No. 60/165,578 filed Nov. 15, 1999.

FIELD OF THE INVENTION

The invention is directed to nasal support devices for animals. Specifically, the invention provides devices, components and methods for reusable nasal support devices for animals.

BACKGROUND OF THE INVENTION

Nasal support devices for supporting tissues overlying the nasal passages of an animal are known and disclosed in, for example, U.S. Pat. No. 5,913,873 and PCT Publication No. US98/07885. Other nasal support devices for animals are disclosed in copending U.S. application Ser. Nos. 09/264,464 and 09/379,425. One currently available nasal support device for animals is the FLAIR™ Equine Nasal Strip available from CNS, Inc., Bloomington, Minn.

Systems and methods for reusing human nasal dilators have been disclosed in, for example, U.S. Pat. Nos. 5,842,469 and 5,957,126.

The disclosures of each of the foregoing patents and patent applications are incorporated herein by reference.

SUMMARY OF THE INVENTION

The present invention provides nasal support devices and methods for supporting the unsupported nasal tissues of an animal. In preferred embodiments, the invention provides reusable nasal support devices and reuse engaging layers providing for reuse of nasal support devices.

Throughout the specification, guidance may be provided through a list of examples. In each instance, the referred to list serves only as a representative group. It is not meant, however, that the list is exclusive.

DETAILED DESCRIPTION OF THE INVENTION

Figure 1:
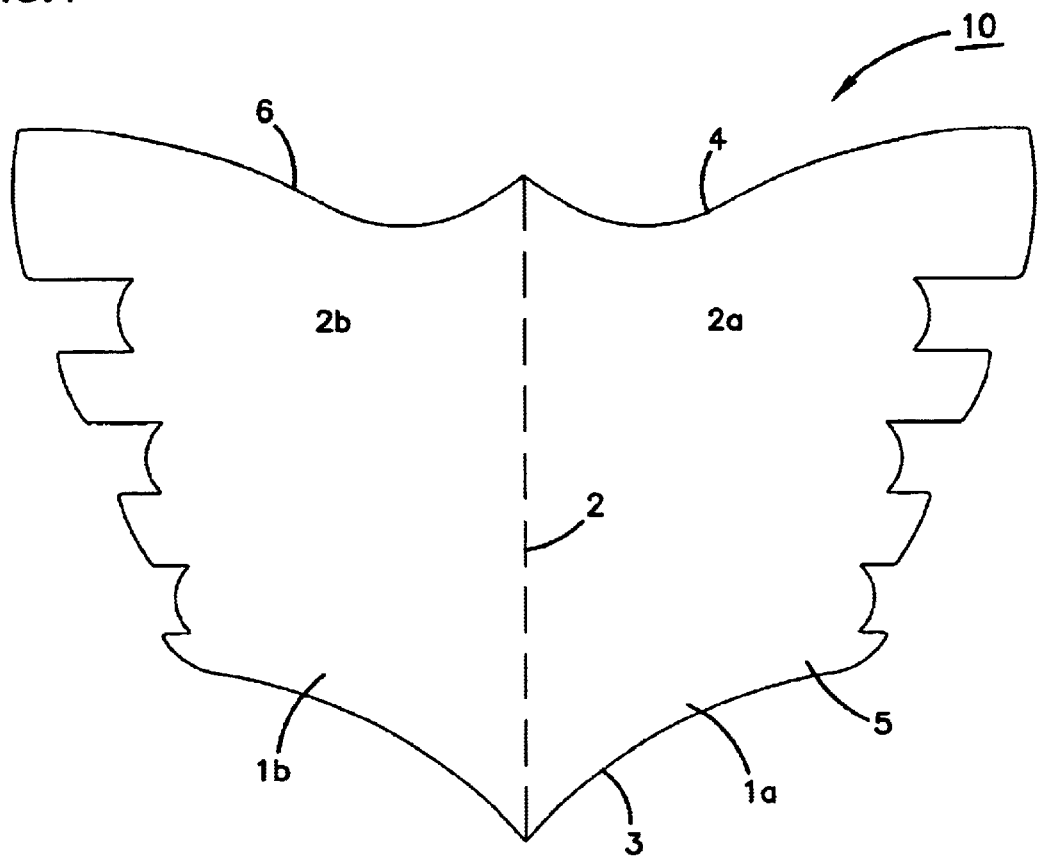
FIG. 1 is a top plan view of one embodiment of a reuse engaging layer according to the invention, the bottom plan view being substantially identical.

The present invention is directed to reusable nasal support devices for animals. As used herein, the term "animals" includes animals as disclosed in U.S. Pat. No. 5,913,873, PCT Publication No. US98/07885 and copending U.S. Ser. Nos. 09/264,464 and 09/379,425. The term "reusable" refers to a nasal support device which can be applied to an animal, removed and subsequently reapplied to the same or a different animal. Typically, a nasal support device provides for a single use, that being the time from adhesion to an animals nose until removal of the device from the nose, for whatever reason.

In one embodiment, a reusable nasal support device can be prepared by application of a reuse engaging layer to the spent engaging layer of a previously used nasal support device. As used herein, "spent engaging layer" refers to the engaging layer used to adhere a nasal support device to an animal after the nasal support device has been removed from the animal. The "reuse engaging layer" provides an adhesive layer for reattaching the nasal support device to an animal's nose after an earlier engaging layer is spent. Nasal support devices which can be used according to this embodiment of the invention include, for example, any of the nasal support devices for animals disclosed in the above recited patents and patent applications, or, for example, the FLAIR™ Equine Nasal Strip available from CNS, Inc. Suitable reuse engaging layers include, for example, double-sided tape or transfer adhesives such as No. 1524 transfer adhesive available from 3M Co., St. Paul, Minn.

According to this embodiment, subsequent to application of a nasal support device to an animal, the nasal support device can be removed from the animal and a reuse engaging layer applied to the spent adhesive surface of the engaging layer which previously was in contact with the nose of the animal. The reuse engaging layer is applied to the previously used nasal support device after removal from the animal. However, it will be appreciated that if the engaging layer becomes non-functional (spent) due to the adhesive surface being spent as a result of adhesion or other contact with something other than the nose of an animal, nonetheless, the reuse engaging layers and methods disclosed herein can be used for preparing a reusable nasal support.

When a double-sided tape is used, the adhesive of each side of the tape may be the same or different. For example, one side of the double-sided tape can include an adhesive which provides a high peel resistance from the engaging layer of the previously used nasal support device and the second side of the double-sided tape can include an adhesive which provides an appropriate peel resistance from the animal's nose when applied to the nose. In general, the reuse engaging layer can be applied to a used nasal support device immediately after removal of the nasal support device from an animal. In an alternative embodiment, the nasal support device can be removed from the animal and a period of time allowed to pass before application of the reuse engaging layer applied to the nasal support device. In a preferred embodiment, the reuse engaging layer is not applied to the used nasal support device for at least three hours, typically at least 12 hours and in a preferred embodiment at least 24 hour after removal of the used nasal support device from an animal.

It is foreseen that a nasal support device can be used multiple times and thus include a plurality of reuse engaging layers applied to the nasal support device with or without a reuse of the nasal support device between application of each subsequent reuse engaging layer.

It is also foreseen that in an alternative embodiment, rather than using a transfer adhesive tape or double-sided tape, a single-sided tape can be used. According to this embodiment, one side of the single-sided tape includes an adhesive for adhering the used nasal support device to an animal's nose. The second side of the single-sided adhesive tape does not include an adhesive. Thus, a liquid adhesive can then be applied to the engaging surface of the nasal support device or to the non-adhesive side of the single-sided tape, or both, and the single-sided tape mounted onto the spent engaging layer of the nasal support device. The adhesive side of the single-sided tape faces away from the spent engaging layer.

Preferably, the configuration of a single or double-sided tape or transfer adhesive is pre-cut to substantially the same shape as that of the nasal support device on which the reuse engaging layer will be applied. However, the configuration of the reuse engaging layer can alternatively be packaged in a rectangular, square, circular, oval or other shape and cut to the desired shape close to the time of application of the reuse engaging layer to the nasal support device.

In an alternative embodiment, a reusable nasal support device for animals can include one or more components as disclosed in the foregoing patents and patent applications with a reusable engaging layer. According to this embodiment, the engaging layer can comprise an adhesive system which permits reapplication of a nasal support device to an animal after the nasal support device has previously been used on the same or a different animal without addition of a new engaging layer. One example of such a reusable adhesive which is suitable for this embodiment of the invention is a fibrous pressure-sensitive adhesive layer comprising an entangled web of pressure-sensitive adhesive fibers such as disclosed in U.S. Pat. No. 5,957,126, the entire disclosure of which is incorporated herein by reference.

Referring now to FIGS. 1–4, examples of some configurations of a reuse engaging layer and device suitable for use with the illustrated reuse engaging layers as shown. FIG. 1 is a top plan view of one embodiment of a reuse engaging layer 10 according to the invention. The bottom plan view of reuse engaging layer 10 is substantially identical to the top plan view illustrated. The side views are essentially void of any particular configurational features. In the illustrated embodiment, the reuse engaging layer 10 includes a first side piece 1a and a second side piece 1b that intersect at the midline 2 of the midline region 2a and 2b. In use the rostral end 3 is oriented toward the apex of the animal's nose and the caudal end 4 is oriented towards the eyes of the animal. The rostral end 3 and caudal end 4 align with the rostral end and caudal end of a nasal support device 20 as illustrated, for example, in FIG. 2.

The midline region has a midline dimension extending from the rostral end to the caudal end. As shown in FIGS. 1–4, the midline dimension is typically longer than side piece dimensions of the first and second side pieces 1a, 1b. The device also includes a transverse dimension. The "transverse dimension" is defined as the length of the device from the peripheral edge of one side of the device to the peripheral edge of the second side of the device. The transverse dimension can be approximately equal at the rostral and caudal edge. Alternatively, the transverse dimension can vary in a single device depending if measured, for example, along the caudal edge, the rostral edge, the narrowest part or the widest part. In one embodiment configured for an average size horse, the transverse dimension at the narrowest part can be about 5–12 cm and about 10–17 cm at the widest part.

Figure 2:
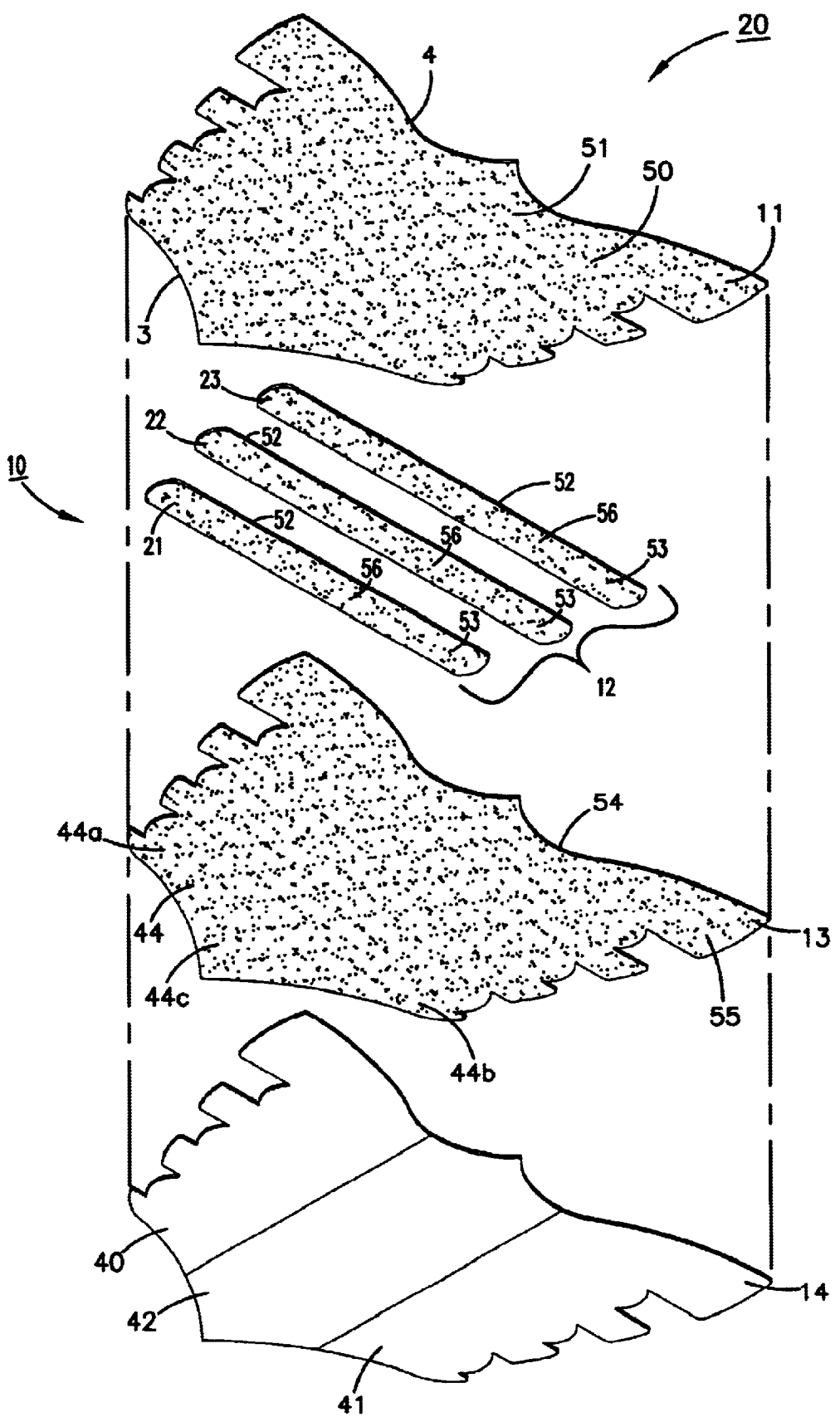
FIG. 2 is an exploded perspective view of one embodiment of a nasal support device for use with the reuse engaging layer of FIG. 1.

In FIG. 2, nasal support device 20 includes a surface layer 11, support layer 12, engaging layer 13, and release liner 14. A carrier layer is not shown in this view. Reuse engaging layer 10 can be a transfer adhesive or double or single-sided tape as discussed above. The reuse engaging layer 10 can include a release liner 14 on either the top side, the bottom side, or both, that is similar to release liner 14 in FIG. 2. Materials for suitable release liners are known.

In the illustrated embodiment, release liner 14 comprises three components, first lateral piece 40, second lateral piece 41, and an intermediate piece 42. As described above, after engaging layer 13 has been spent, a reuse engaging layer 10 can be positioned directly over engaging layer 13. As discussed, the top surface 5 of reuse engaging layer 10 can be applied to engaging layer 13 and the bottom surface 6 adhered to the animal's nose.

Other aspects of a nasal support device suitable for a reusable nasal support device of the invention will be described. For example, in the embodiment of FIG. 2, the bottom side 50 of surface layer 11 (i.e., the side towards the animal's nose when in use) can include an adhesive layer 51 to adhere the surface layer 11 to the top side 52 of lift members (21, 22, 23) and to the top side 54 of engaging layer 13. The bottom side 53 of lift members (21, 22, 23) can include an adhesive 56 to adhere the lift members (21, 22, 23) to the top side 54 of the engaging layer. The bottom side 55 of engaging layer 13 includes adhesive 44 to adhere the device to the animal's nose. Each of the adhesives of NSD 20 can be a coated medical tape, transfer adhesive, liquid adhesive, PSA, etc. In one preferred embodiment, the surface layer 11 is 9910 black non-woven medical tape available from 3M Co., St. Paul, Minn, the lift members 21, 22, 23 are MYLAR® available from DuPont Films, Wilmington, Del., the engaging layer 13 is DM-2009, available from Dermamed, Pallmadge, Ohio 44278 and the release liner is DM-2009 release liner, also available from Dermamed.

Figure 3:
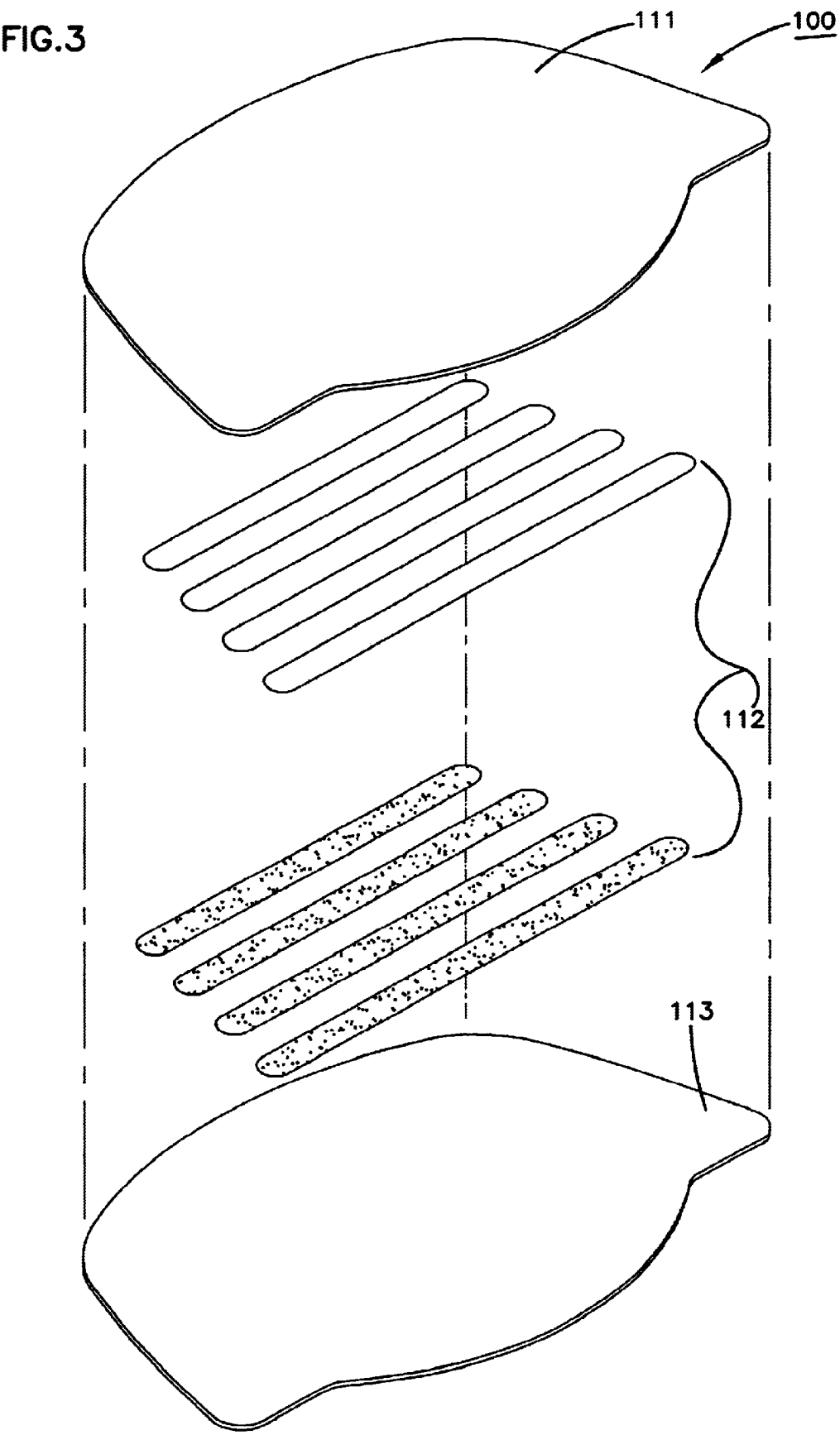
FIG. 3 is an exploded perspective view of an alternative embodiment of a nasal support device suitable for use with a reuse engaging layer of the invention.

FIG. 3 illustrates an exploded perspective view of an alternative embodiment of nasal support device 100 according to the invention. In this embodiment, nasal support device 100 includes a surface layer 111, support layer 112, and engaging layer 113.

Figure 4:
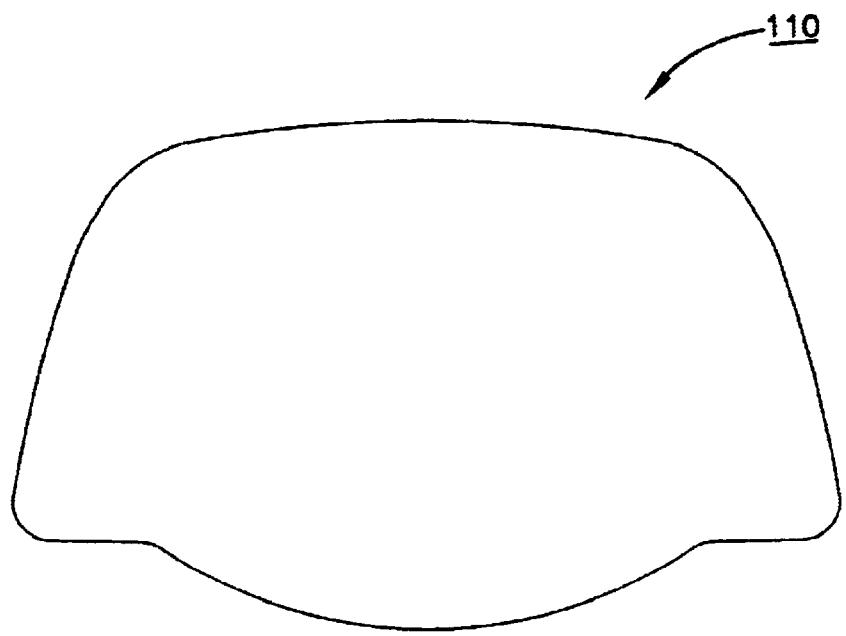
FIG. 4 is a top plan of a reuse engaging layer suitable for use with the nasal support device of FIG. 3, the bottom plan view being substantially identical.

FIG. 4 illustrates a top plan view of a reuse engaging layer 110 particularly advantageous for use with nasal support device 100. A bottom plan view of reuse engaging layer 100 is substantially identical to the top plan view. The side views are essentially void of configurational features. Reuse engaging layers 10 and 110 can include any of the above-described features of a reuse engaging layer.

From the foregoing detailed description and examples, it will be evident that modifications and variations can be made in the devices and methods of the invention without departing from the spirit or scope of the invention. Therefore, it is intended that all modifications and verifications not departing from the spirit of the invention come within the scope of the claims and their equivalents.

We claim:

1. A reusable nasal support device for use on an animal, the reusable nasal support device comprising:
   a support layer configured and sized for use on an animal;
   a first engaging layer for adhesively securing the nasal support device to the nose of an animal; and
   a second engaging layer for adhesively securing the nasal support device to an animal after the first engaging layer is spent;
   wherein at least the first engaging layer includes:
      a rostral end and a caudal end;
      a midline region having a midline dimension extending from the rostral end to the caudal end;
      a first side piece and a second side piece that intersect at the midline region, each side piece having a side piece dimension extending from the rostral end to the caudal end;
      the midline dimension being longer than the side piece dimensions; and
      a tranverse dimension generally perpendicular to the midline dimension and extending from a peripheral edge of the first side piece to a peripheral edge of the second side piece, the transverse dimension being about 10 cm to about 17 cm.

2. The reusable nasal support device according to claim 1 wherein the second engaging layer is applied to the nasal support device after the first engaging layer has been adhesively secured and removed from the nose of an animal.

3. The reusable nasal support device according to claim 1 wherein the first engaging layer is a double-sided tape.

4. The reusable nasal support device according to claim 1 wherein the second engaging layer is a double-sided tape.

5. The reusable nasal support device according to claim 1 wherein the second engaging layer is a single-sided tape.

6. The reusable nasal support device according to claim 1 wherein the second engaging layer is a transfer adhesive tape.

7. The reusable nasal support device according to claim 1 further comprising three or more engaging layers.

8. A method for supporting vestibular tissues overlying a nasal passage of a first animal, the method comprising a step of:
adhesively applying a nasal support device to the tissues overlying the nasal passages of the first animal, the nasal support device including a support layer configured and sized for use on the first animal, and a first engaging layer, the first engaging layer including:
a rostral end and a caudal end;
a midline region having a midline dimension extending from the rostral end to the caudal end;
a first side piece and a second side piece that intersect at the midline region, each side piece having a side piece dimension extending from the rostral end to the caudal end;
the midline dimension being longer than the side piece dimensions; and
a tranverse dimension generally perpendicular to the midline dimension and extending from a peripheral edge of the first side piece to a peripheral edge of the second side piece, the transverse dimension being about 10 cm to about 17 cm;
removing the nasal support device from the first animal;
applying a second engaging layer to the nasal support device after removal from the first animal; and
applying the nasal support device including the second engaging layer to a nose of a second animal.

9. The method according to claim 8 wherein the first animal is the same as the second animal.

10. An adhesive structure for adhesively re-securing a nasal support device to an animal after the nasal support device has been removed from an animal, the adhesive structure comprising:
an adhesive member configured and sized for use on an animal, the adhesive member including a first engaging surface and an opposite second engaging surface, the first engaging surface having a first adhesive layer for adhesively securing the first engaging surface to the nasal support device, the second engaging surface having a second adhesive layer for adhesively securing the opposite second engaging surface to an animal, after the nasal support device has been applied and removed from an animal; the adhesive member including:
a rostral end and a caudal end;
a midline region having a midline dimension extending from the rostral end to the caudal end;
a first side piece and a second side piece that intersect at the midline region, each side piece having a side piece dimension extending from the rostral end to the caudal end;
the midline dimension being longer than the side piece dimensions; and
a tranverse dimension generally perpendicular to the midline dimension and extending from a peripheral edge of the first side piece to a peripheral edge of the second side piece, the transverse dimension being about 10 cm to about 17 cm.

11. The adhesive structure according to claim 10 wherein the adhesive member is configured and sized for use on a horse.

12. The reusable nasal support device according to claim 1 wherein the engaging layer is configured and sized for use on a horse.

\* \* \* \* \*